US012434007B2

(12) United States Patent
Jugl et al.

(10) Patent No.: US 12,434,007 B2
(45) Date of Patent: Oct. 7, 2025

(54) INJECTION DEVICE

(71) Applicant: Sanofi, Paris (FR)

(72) Inventors: Michael Jugl, Frankfurt am Main (DE); Michael Helmer, Frankfurt am Main (DE); Steffen Raab, Frankfurt am Main (DE); Martin Vitt, Frankfurt am Main (DE)

(73) Assignee: Sanofi, Paris (FR)

( * ) Notice: Subject to any disclaimer, the term of this patent is extended or adjusted under 35 U.S.C. 154(b) by 1115 days.

(21) Appl. No.: 17/421,661

(22) PCT Filed: Jan. 17, 2020

(86) PCT No.: PCT/EP2020/051122
§ 371 (c)(1),
(2) Date: Jul. 8, 2021

(87) PCT Pub. No.: WO2020/148426
PCT Pub. Date: Jul. 23, 2020

(65) Prior Publication Data

US 2022/0088313 A1 Mar. 24, 2022

(30) Foreign Application Priority Data

Jan. 18, 2019 (EP) .................................... 19305066

(51) Int. Cl.
*A61M 5/315* (2006.01)

(52) U.S. Cl.
CPC ...... *A61M 5/3157* (2013.01); *A61M 5/31551* (2013.01); *A61M 5/31553* (2013.01);
(Continued)

(58) Field of Classification Search
CPC ............ A61M 5/3157; A61M 5/31551; A61M 5/31553; A61M 5/31558; A61M 5/31585;
(Continued)

(56) References Cited

U.S. PATENT DOCUMENTS 5,582,598 A * 12/1996 Chanoch ........... A61M 5/31585 604/218
6,090,081 A 7/2000 Sudo et al.
(Continued)

FOREIGN PATENT DOCUMENTS

CN 102325562 1/2012
CN 105102039 11/2015
(Continued)

OTHER PUBLICATIONS

International Preliminary Report on Patentability in International Appln. No. PCT/EP2020/051122, dated Jun. 16, 2021, 8 pages.
(Continued)

*Primary Examiner* — Kevin C Sirmons
*Assistant Examiner* — Leah J Swanson
(74) *Attorney, Agent, or Firm* — Bond, Schoeneck & King, PLLC

(57) ABSTRACT

An injection device including a housing, a dose indicator, and a release mechanism. The dose indicator is positioned within the internal space of the housing and includes a number of engaging members at least one thereof being configured to contact multiple of distinct ratchet features in course of a helical or screwing movement in distinct positions to provide a user with a tactile indexing appearance in the way of an increased or decreased dwelling torque at each of the multiple distinct positions. The release mechanism is connected to the dose indicator and includes a drive member. The release mechanism is configured to, when activated during dose dispense, urge the engaging members away from the distant position and against the force of the resilient bias thereby suspending the indexing ratchet appearance at least for a subset of the multiple distinct positions.

22 Claims, 7 Drawing Sheets

(52) U.S. Cl.
CPC .... *A61M 5/31558* (2013.01); *A61M 5/31585* (2013.01); *A61M 2205/582* (2013.01)

(58) Field of Classification Search
CPC .......... A61M 5/31561; A61M 5/31556; A61M 5/24; A61M 5/315; A61M 5/31525; A61M 5/31526; A61M 5/31528; A61M 5/31533; A61M 5/31535; A61M 5/31545; A61M 5/31548; A61M 5/3155; A61M 5/31555; A61M 5/3156; A61M 5/31563; A61M 5/31565; A61M 5/31566; A61M 5/31576; A61M 5/31575; A61M 5/3158; A61M 5/3159; A61M 5/31591; A61M 5/31593; A61M 2205/582; A61M 2205/585
See application file for complete search history.

(56) References Cited

U.S. PATENT DOCUMENTS

| | | | | |
|---|---|---|---|---|
| 2012/0046643 | A1* | 2/2012 | Plumptre .......... | A61M 5/31551 604/207 |
| 2021/0386933 | A1* | 12/2021 | Gjoedesen ........ | A61M 5/31591 |

FOREIGN PATENT DOCUMENTS

| | | | |
|---|---|---|---|
| CN | 106794319 | | 5/2017 |
| CN | 106999658 | | 8/2017 |
| CN | 108697859 | | 10/2018 |
| EP | 2190506 | A | 6/2010 |
| EP | 3181171 | | 6/2017 |
| JP | H10-314305 | A | 12/1998 |
| JP | 2012-513266 | A | 6/2012 |
| JP | 2014-083398 | | 5/2014 |
| JP | 2018-537255 | A | 12/2018 |
| WO | WO 1999/038554 | | 8/1999 |
| WO | WO 2010/053569 | | 5/2010 |
| WO | WO 2010/072662 | | 7/2010 |
| WO | WO 2014/166888 | | 10/2014 |
| WO | WO 2016/055620 | | 4/2016 |
| WO | WO 2016/083380 | | 6/2016 |
| WO | WO 2017/102395 | | 6/2017 |
| WO | WO 2019/102027 | | 5/2019 |

OTHER PUBLICATIONS

International Search Report and Written Opinion in International Appln. No. PCT/EP2020/051122, dated Apr. 6, 2020, 11 pages.

* cited by examiner

INJECTION DEVICE

CROSS-REFERENCE TO RELATED APPLICATIONS

The present application is the national stage entry of International Patent Application No. PCT/EP2020/051122, filed on Jan. 17, 2020, and claims priority to Application No. EP 19305066.3, filed on Jan. 18, 2019, the disclosures of which are incorporated herein by reference.

TECHNICAL FIELD

The present disclosure is generally directed to a handheld injection device, i.e. a drug delivery device for selecting and dispensing a number of user variable doses of a liquid drug or medicament formulation.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. Further, so called fixed dose devices which only allow dispensing of a predefined dose without the possibility to increase or decrease the set dose are known.

There are basically two types of drug delivery devices: refillable devices (i.e., reusable) and non-refillable (i.e., disposable) devices. For example, disposable pen delivery devices are supplied as self-contained drug device combinations. Such self-contained drug device combinations do not have removable pre-filled cartridges. Rather, the pre-filled cartridges cannot be removed or replaced from these devices without destroying or at least causing significant damage to the device. The present disclosure is applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. In general, the present disclosure is applicable for all of these types of devices, i.e. for devices with or without a drive spring.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medicament (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or lead screw (piston rod) contained within the dose setting mechanism presses against the bung or stopper of the cartridge. This force causes the medicament contained within the cartridge to be injected through an attached needle assembly. After an injection, as generally recommended by most drug delivery device and/or needle assembly manufacturers and suppliers, the needle assembly is removed and discarded.

Documents U.S. Pat. No. 5,582,598 and WO 2010/053569 A1 disclose an injection device which comprises a housing and a dose sleeve which provides a groove at its outer surface. The housing comprises a pin which directly meshes with the groove of the dose sleeve. The groove of the dose sleeve comprises sections with different pitch for providing a different dose dialing and dispensing feeling caused by different application forces with regard to each pitch section. However, the rotation angle with regard to one dose unit is the same for each section of the groove.

Document WO 99/38554 A1 refers to an injection syringe comprising a piston rod and a piston rod drive comprising a piston rod guide and a nut member and a dose setting mechanism with a thread connection along which an injection button by rotation of a dose setting element relative to the housing is screwed out from the proximal end of the housing, wherein axial pressing of the injection button transforms the axial movement to a rotation of one of the piston rod drive elements relative to the other. Further, a unidirectional coupling is provided between the nut member and the piston rod guide allowing rotation of these parts relative of each other in one direction but not in the opposite direction, the allowed rotation being one by which the piston rod is transported in a distal direction in the syringe, the coupling being so designed that a set initial reluctance has to be overcome before the rotation takes place. Additionally, a click coupling is disclosed providing a moderate resistance against rotation between the housing and the element rotated relative to the housing to set a dose. Thereby it is ensured that the positon corresponding to a set dose is maintained and is not inadvertently altered. The clicks may be taken as an audible signal indicating the size of the set dose.

Document US 2012/0046643 A1 describes an injection device for administration of a fixed dose comprising a housing and a dosing element, wherein the user rotates a dosing element in a dose setting direction resulting in a helical movement of the dosing element defined by a position of an engaging feature relative to an inner thread of the housing. By an interaction of the engaging feature with a detent of the thread the user is informed that a dose has been set, wherein the detent gives an audible or tactile signal when the engaging feature passes the detent. Document EP 3 181 171 A1 discloses a drive mechanism for an injection device with a display member and a dose member. Each specific dose size actually set by dialing the display member and the dose member correlates to a well-defined position of blocking elements along a helical path of a blocking structure.

Over the last decades, the amount of medicament needed by a typical patient within one dose has changed. Recently, the average weight of the patients has increased so that the effective dose size of a medicament has increased as well. This is why effective dose size in many cases goes with the weight of the patient. Accordingly, if the effective concentration of the medicament is not changed, the medicament containers (e.g. cartridges) need to become bigger. As this results in a bigger size of injection devices or higher costs with regards to the container material, which is disliked by the patients and pharma industry, often the concentration of the effective medicament was enhanced to overcome the above-mentioned problem. However, with a higher concentration of the effective medicament and it becomes more difficult to dial and dispense low doses of the medicament with acceptable accuracy. Further, patients wish to receive audible and tactile signals informing about dose increase and decrease.

SUMMARY

The present disclosure provides an improved injection device with high accuracy during dose dialing and dispensing. The injection devices presented herein may be compact in size.

In a first aspect, an injection device according to a first principle concept disclosed and explained herein comprises:

- a housing defining an internal space with an inner surface, the inner surface being provided with a thread feature and a multiple of distinct ratchet features spread along a helical path,
- a dose indicator positioned within the internal space of the housing, the dose indicator having an external surface configured to mesh or engage with the thread feature for restricting the motional freedom of the dose indicator within the housing to follow a helical or screwing movement during dose dialing and dose dispensing, the dose indicator further comprising a number of engaging members at least one thereof being configured to contact the multiple of distinct ratchet features in course of the helical or screwing movement in distinct positions, wherein the contact is configured to provide a user with a tactile indexing appearance in the way of an increased or decreased dwelling torque at each of the multiple distinct positions.

During dose dialing the rotation of a dose dial grip coupled to the dose indicator is transferred to the dose indicator such that the dose indicator travels along the helical path, wherein the rotation angle of the dose indicator with regard to an initial position of the dose indicator represents the dialed dose. During dose dialing the engaging member gets in contact with several of the multiple ratchet features, which may be provided as a teething with a plurality of equally spread gear teeth or saw teeth or other form of pointed or rounded teeth. In instances, the resolution or pitch of the regular teething may be selected to match with the discrete dose setting positions of the device. For example, one ratchet feature may be provided for every dose increment, for example per unit or half unit of insulin. Alternatively, a reduced set of selectable dose values may be reflected by a respectively reduced number or ratchet features. The advantage of providing the ratchet feature in the large diameter of the housing inner surface can be seen in a very clear indexing perception. Moreover, the non-overlapping layout of the ratchet features along a unique path of travel provides rich freedom for tailoring the ratchet appearance to the recommended dosing regimen of the respective rug to be expelled. Further, according to the first embodiment, the engaging member may be configured to at least partially disengage from the teething during dose dispensing which helps avoiding torque loss. This means, for example, that the device comprises a release mechanism provided in connection with the dose indicator, the release mechanism being configured to, when activated during dose dispense, urge the number of engaging members away from the distant position against the force of the resilient bias thereby suspending the indexing ratchet appearance at least for a subset of the multiple distinct positions.

Additionally, the injection device may have all or some of the ratchet features integrated with the thread feature in the housing, in particular as a profiled a crest line or shoulder of a helically extending thread rib.

The engaging member may comprise at least one tooth or cog configured to engage or mate with the ratchet features. The engaging member may be adapted to allow deflection away from this engagement or mating situation. This may be used to configure the mechanism such that the dose indicator provides the indexing appearance only during dose setting or canceling operation. This may be such that the dose indicator is coupled with regard to the housing such that when the dose indicator is rotated during dose dialing the rotational movement is provided in discrete steps only and not continuously, for example in steps covering a full or a half unit of a medicament dose.

At least partial disengagement of the engaging member from the ratchet features means that it may be fully disengaged or the engagement may be less strong during dose dispensing (e.g. during dose dispensing the engaging member does not penetrate as deeply as during dose dialing into the notches of the toothing). In one embodiment the partial disengagement may be adapted such that the residual torque loss caused by the ratchet connection is small but the user still slightly feels the engagement.

The housing and the dose indicator (dose dial sleeve) of the injection device may have a hollow cylindrical (sleeve-like or tubular) form. According to the above embodiment the housing and the dose indicator may be threaded to be engaged so that the dose indicator moves helically with regard to the housing during dose dialing and dispensing. For providing an medicament to a patient in the first step a predefined or user selectable dose is dialed by the patient and in the second step the patient dispenses the dialed dose, for example by injection with a needle attached at the distal end of the housing. In one embodiment the fluid medicament is contained within a cartridge attached to the housing or accommodated within the housing. The cartridge comprises a bung at its proximal end which is connected to the distal end of the lead screw (piston rod) such that a distal axial movement of the lead screw drives the bung of the cartridge into distal direction thereby expelling the medicament from the cartridge. The dose injection may be facilitated by a user pressing an injection button which is coupled with the dose indicator.

According to one embodiment

- a drive member located within the dose indicator and comprising a first sleeve-like element (also called bushing in the following) which is axially displaceable relative to the dose indicator during dose dispensing,
- wherein the first sleeve-like element of the drive member is adapted to pivot the at least one pivotable engaging member during dose dispensing by an axial displacement relative to the dose indicator in order to at least partly disengage the pivotable engaging member from the toothing of the thread, wherein the first sleeve-like element is displaced against an axial force of a biasing member. This embodiment provides a simple possibility to disengage at least partly the pivotable engaging member from the toothing of the thread. In one embodiment the pivotable engaging member is kept with its proximal end within a notch of a ring comprising a plurality of notches at the inner surface of the dose indicator. The first sleeve-like element may be coaxially accommodated within the dose indicator. In one embodiment the term "during dose dispensing" means the time period in which the injection button is pressed by the user. As soon as the injection button is pressed the first sleeve-like element coupled to the injection button is displaced axially thereby rotationally coupling the dose indicator and the first sleeve-like element. The biasing member may be a compression spring or at least one Belleville spring washer.

In one embodiment the first sleeve-like element comprises longitudinal grooves, for example at its distal end, which engage projecting teeth provided at the inner surface of the dose indicator during dose dispensing in order to be rotationally fixed with regard to the dose indicator and thereby rotate together with the dose indicator during dose dispense.

In one embodiment the dose indicator rotates relative to the first sleeve-like element during dose dialing. The first sleeve-like element is coupled to a lead screw, wherein the lead screw does neither rotate nor translate axially during dose dialing. In one embodiment the first sleeve-like element is coupled to the lead screw via a second sleeve-like element, wherein the second sleeve-like element and the lead screw are coupled by a splined connection, for example a pin moving along a groove running in axial (longitudinal) direction. The second sleeve-like element does neither rotate nor translate during dose dialing, wherein the first sleeve-like element translates axially relative to the second sleeve-like element during dose dialing. In one embodiment the first sleeve-like element and the second sleeve-like element together may form a drive member.

In one embodiment the dose indicator further comprises at least one second pivotable member, wherein the at least one second pivotable member may be located, for example, essentially opposite to one pivotable engaging member or two pivotable engaging members with regard to the cross section of the dose indicator, wherein the second pivotable member is adapted to support the first sleeve-like element during axial displacement of the first sleeve-like element relative to the dose indicator. This support avoids a rocking movement of the first sleeve-like element or its jamming within the dose indicator. In one embodiment the second pivotable member may be kept with its proximal end within the notch of a ring comprising a plurality of notches/grooves and teeth (between the notches/grooves) at the inner surface of the dose indicator.

In one embodiment the at least one pivotable engaging member has a suitable and wing-like form, which is easy and cost effective in production, wherein the wing-like form comprises at least one of the following features:

- the wing-like form is attached to the dose indicator by a neck portion, wherein a pivot axis may be located at the neck portion,
- a side surface of the wing-like form oriented radially outwards is adapted to engage the toothing of the thread,
- a sloping surface at the proximal end of the wing-like form is adapted such that a corresponding sloping surface at the distal end of the first sleeve-like element engages the sloping surface of the wing-like form during dose dispense and after axial displacement of the first sleeve-like element thereby pivoting the pivotable engaging member in an easy way. For example, the side surface of the wing-like form comprises a tooth or cog wherein the tooth or cog projects from the side surface and/or is adapted to engage the toothing of the thread.

In one embodiment the toothing of the thread comprises a first section with a first profile form and a second section with a second profile form, wherein the first profile form is different from the second profile form. For example, the thickness of each tooth or the pitch (i.e. the thickness of one tooth and the width of one neighboring groove), each measured along the thread, or the form of the teeth or the grooves is different in the first section and the second section. Alternatively or additionally, the height of each tooth is different in the first section and the second section. Using the different profile forms the toothing may be tailored to the needs of the patient and/or the injection device in an easy and cost effective way. For example, the toothing may be adapted such that it allows tactile engagement only in a predefined section of the thread thereby indicating to the user that only medicament doses corresponding to the predefined section of the thread are allowed to be dialed.

According to one embodiment a drive member may effect a change in the transformation ratio between the rotation and the longitudinal shift of the dose indicator relative to the housing such that within a first rotation angle section the rotation of the dose indicator is transformed with a first transformation ratio and within at least a second rotation angle section the rotation of the dose indicator is transformed with a second transformation ratio, wherein the (absolute) rotation angle of the dose indicator is measured from an initial position of the dose indicator.

According to one embodiment the drive member of the injection device provides a change in the conversion ratio when the dose indicator is rotated within a second rotation angle section measured from the initial position of the dose indicator compared with the first rotation angle section. The initial position is the zero dose position which is taken by the dose indicator prior dose dialing. The transformation ratio change provides the possibility to dial the dose within a first rotation angle section with a different resolution (higher or smaller) than in a second rotation angle section. The transformation change also occurs during dose dispensing (injection) but vice versa. The rotation angle is the absolute rotation angle which may be higher than 360°. In one embodiment the first rotation angle section refers to smaller rotation angles than the second rotation angle section. For example, the first rotation angle section is from the initial position until a rotation angle of 360° of the dose indicator and the second rotation angle section is from a rotation angle of 360° to 720° or 1080° of the dose indicator. Within one rotation angle section the transformation ratio is identical. The transformation ratio suddenly changes from the first transformation ratio to the second transformation ratio during dose dialing and reverse during dose injection but stays the same within one predefined rotation angle section.

In one embodiment the first transformation ratio is less than the second transformation ratio, for example the first transformation ratio is 1 U/I and the second transformation ratio is 1 U/2*I, wherein 1 U means one revolution of the dose indicator with regard to the housing and I means a predefined length value (unit of length) of the longitudinal (axial) shift of the dose indicator with regard to the housing, wherein 2*I means 2 times I.

In one embodiment the rotation velocity of the dose indicator within the first rotation angle section and the second rotation angle section is identical or approximately identical. This is because the threaded connection of the dose indicator with regard to the housing has the same lead within the first rotation angle section and the second rotation angle section of the dose indicator.

In one embodiment the dose indicator may be rotatably fixed during dose dispense with regard to the first sleeve-like element of the drive member, wherein the drive member may further comprise the second sleeve-like element positioned within the first sleeve-like element, wherein the second sleeve-like element (also called driver tube in the following) may be coupled to the lead screw, and wherein the first sleeve-like element may be coupled to the second sleeve-like element by means of a connection comprising a pin and a groove, wherein the pin may move along the groove during dose dialing and dose dispensing. In one embodiment the first sleeve-like element and the second sleeve-like element may be tubular elements. In a further embodiment the second sleeve-like element may be rotatably fixed with regard to the housing during dose dialing and rotatable with regard to the housing during dose dispensing.

In one embodiment the groove may provide a first pitch (grade, slope) along a first section of the groove and a second pitch (grade, slope) along a second section of the groove, wherein the first pitch may be different from the second pitch. The first section of the groove may correspond to the first rotation angle section of the dose indicator and the second section of the groove corresponds to the second rotation angle section of the dose indicator. Accordingly, in one embodiment the first pitch may be higher than the second pitch, for example, the first pitch may be twice the second pitch. Alternatively, the first pitch may be 45° and the second pitch may be 0° meaning the groove running in parallel to the longitudinal axis of the injection device and the first sleeve-like element or the second sleeve-like element providing the groove. The two elements forming the drive member coupled with a pin-groove connection may be found to provide a cost effective possibility to realize the present concept. If one needs a certain relation with regard to the first and the second transformation ratio, mainly the construction of these two elements needs to be changed with regard to the new relation. A fully new construction of the whole injection device is not necessary. The pin-groove connection between the first sleeve-like element and the second sleeve-like element may be realized such that the first sleeve-like element comprises at least one projecting pin at its inner surface, wherein the second sleeve-like element comprises the same number of grooves at its outer surface. Alternatively, the first sleeve-like element may comprise the groove and the second sleeve-like element may comprise the pin.

In one embodiment, the dose indicator comprises a scale at its surface showing the dialed dose to the user, preferably through a window or opening within the housing. In one embodiment, the scale may be a marking provided along a helical path at the surface of the dose indicator, for example by means printing or laser engraving.

In another embodiment, the scale may comprise a first scale section corresponding to the first rotation angle section and a second scale section corresponding to the second rotation angle section of the dose indicator, wherein the graduation of the first scale section may be different from the graduation of the second angle section. The graduation of the first and the second scale section may correspond to the resolution during dose dialing and dispensing within the respective rotation angle section. The number of scale sections may correspond to the number of rotation angle sections provided by a specific implementation.

In one embodiment, the lead screw may be rotatable coupled with the housing during dose dispensing and axially and rotatably fixed with regard to the housing during dose dialing.

In one embodiment, the injection device comprises a injection button coupled to the dose indicator at its proximal end, wherein the injection button is adapted to be pressed into distal direction for dose dispensing thereby axially displacing the first sleeve-like relative to the dose indicator.

The injection device may comprise a cartridge containing a liquid drug or medicament. In instances, by pressing the injection button a portion thereof may be expelled from the cartridge according to the dialed or pre-set amount. The terms "drug" and "medicament", may refer to a pharmaceutical formulation containing at least one pharmaceutically active compound. More details on particular pharmaceutical formulations may be taken from the disclosure of the co-pending application PCT/EP2018/082640 which, to this extent, shall be included herein by reference.

In one embodiment the injection device may be configured to deliver variable, user-selectable, doses of medicament from a cartridge, via a needle. In a preferred embodiment, the device is disposable. It is delivered to the user in a fully assembled condition ready for first use.

A dose may be set by rotating the dial grip located at the end of the housing and coupled to the dose indicator. Delivery of a dose may be initiated by pressing the injection button and displacing the injection button axially in the distal direction. Dose delivery may continue while the injection button remains depressed, until the complete set dose has been delivered. The mechanism may provide audible, visual and/or tactile feedback both on the setting and delivery of each dose.

BRIEF DESCRIPTION OF THE FIGURES

Non-limiting, exemplary embodiments will now be described with reference to the accompanying drawings, in which.

DETAILED DESCRIPTION

Figure 1A:
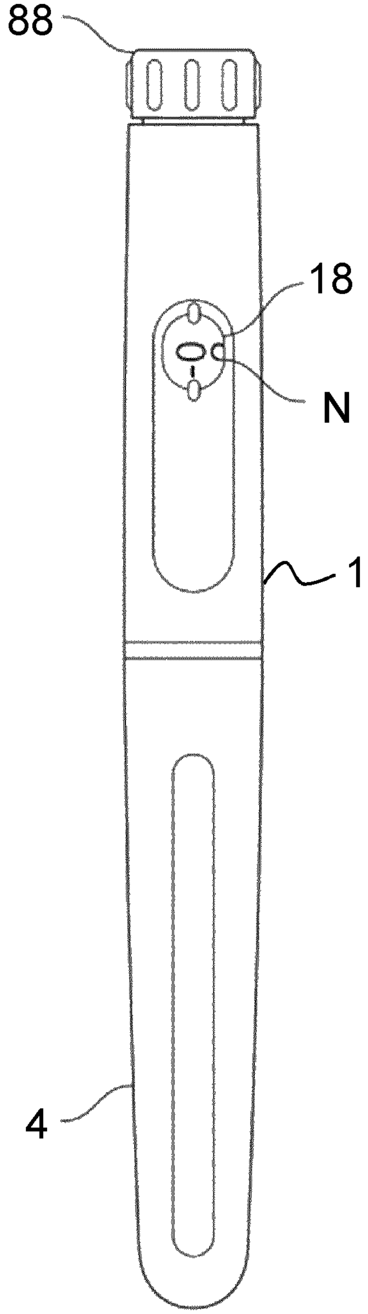
FIG. 1A shows a side view of a first embodiment of an injection device with a cap.
Figure 1B:
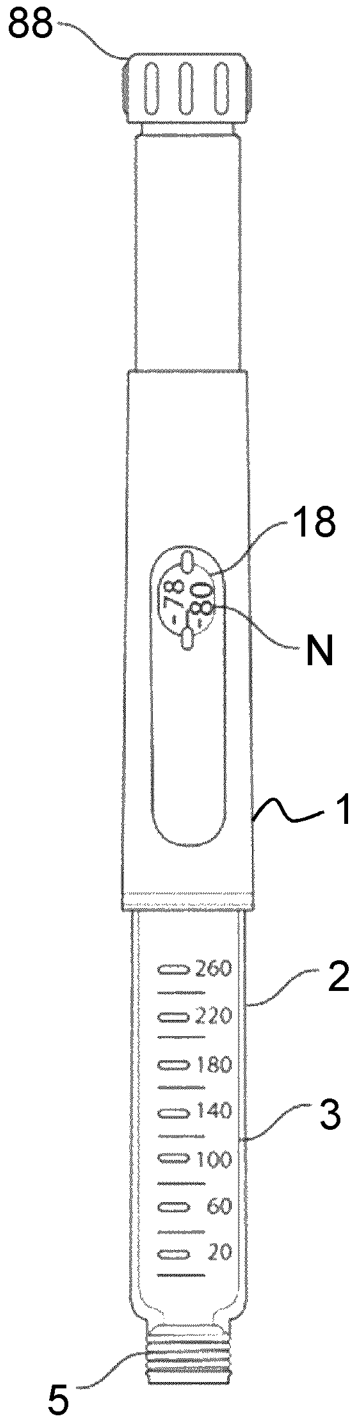
FIG. 1B shows a side view of the injection device of FIG. 1 without cap.
Figure 2:
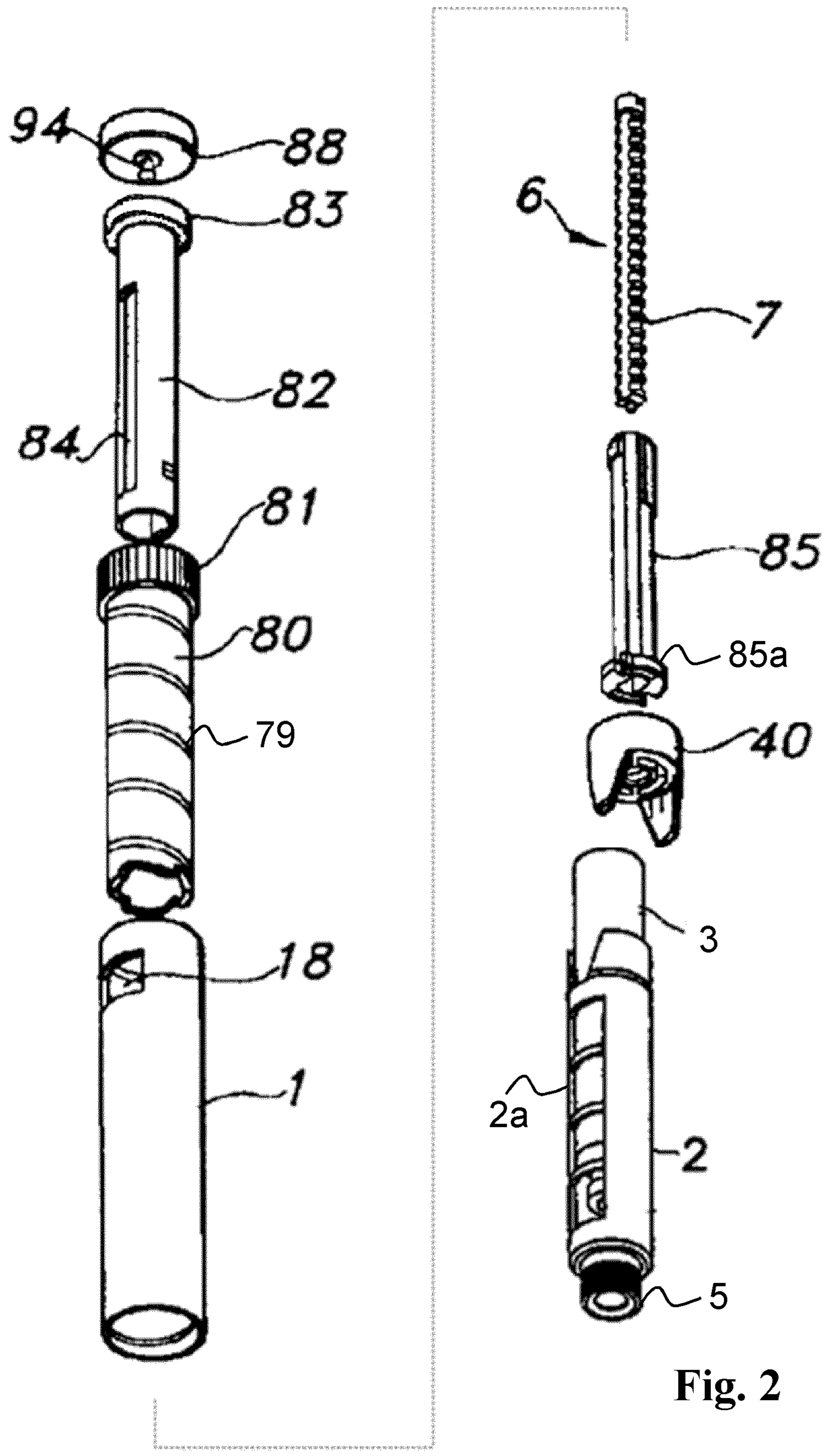
FIG. 2 shows an exploded view of the components of the injection device of FIG. 1.

FIGS. 1A and 1B show a first embodiment of an injection device (drug delivery device) in the form of an injection pen. The device has a distal end (lower end in FIGS. 1A and 1B) and a proximal end (upper end in FIGS. 1A and B). The component parts of the injection device are shown in FIG. 2. All components are located concentrically about a common principal axis (longitudinal axis) of the mechanism. The drug delivery device comprises a body or housing 1, a cartridge holder 2, a cartridge 3, a cap 4, a lead screw (piston rod) 6, an insert 40, a drive member which is a unit consisting of two elements, namely a bushing (first sleeve-like element) 82 and a driver tube (second sleeve-like element) 85 (collectively, with an injection button, the release mechanism), a dose indicator (number sleeve) 80, a dial grip 81, and an injection button 88.

A needle arrangement (not shown) with a needle hub and a needle cover may be provided as additional components, which can be exchanged as explained above. The needle arrangement may be attached to the distal end of the cartridge holder 2, for example by a thread 5 (see FIGS. 1B and 2).

The removable cap 4 fits over the cartridge holder 2 and is retained via clip features to the cartridge holder 2 or the housing 1 (see FIG. 1A).

The housing 1 is a generally tubular component which provides location for the liquid medication cartridge 3 and the cartridge holder 2 which is attached to the housing 1 or integral with it. The cartridge holder 2 receives cartridge 3. A slot or window 2*a* is provided through which the cartridge 3 can be viewed.

One window (through going opening) 18 is provided extending in the longitudinal direction of the housing 1. Through window 18 the dose number N of a scale provided on the outer surface of the dose indicator 80 can be viewed. In one embodiment, the window 18 may be covered by a transparent layer or may comprise a transparent lens in order to magnify the shown dose number N.

The lead screw 6 has an external thread 7 and is rotationally constrained to driver tube 85 via a splined interface. When rotated, the lead screw 6 is forced to move axially relative to the housing 1, through its threaded interface with the insert 40 using thread 7 of the lead screw 6. The lead screw 6 acts on a bung within the liquid medicament cartridge 3 such that the medicament is driven out of the cartridge 3.

The insert 40 is axially and rotationally fixedly attached to the housing 1, for example within the distal end of the housing 1.

The tubular bushing 82 having a flange 83 at its proximal end fits into the dose indicator 80 and over the driver tube 85. The bushing 82 has, for example, two pins 101 projecting from its inner wall engaging grooves 100 of the driver tube 85 whereby the bushing 82 and the driver tube 85 are coupled to each other so that rotation is transmitted between said two elements based on the form of the groove 100 as explained in detail below. Providing only one pin 101 or three or more pins 101 is possible as well.

The driver tube 85 is a tubular element which comprises, for example, two grooves 100 running in axial (longitudinal) direction at its outer surface. The number of grooves 100 corresponds to the number of pins 101 of the bushing 82.

Figure 2B:
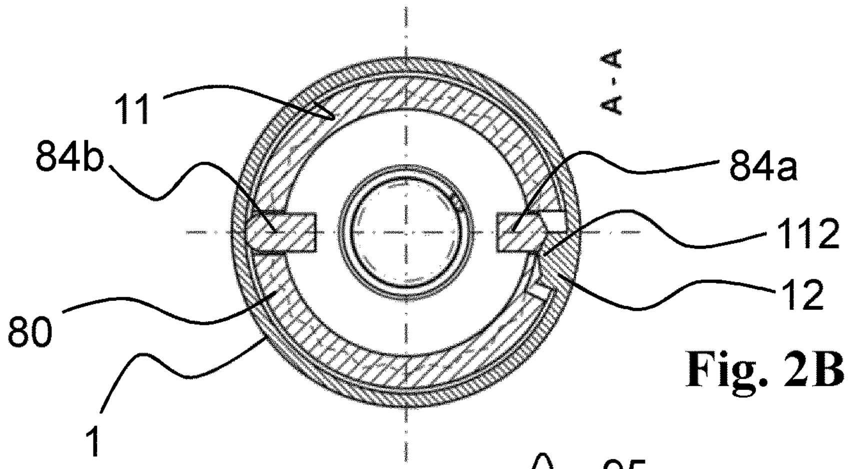
FIG. 2B shows a cross section of the injection device of FIG. 1 during dose dialing (see A-A in FIG. 2A)
Figure 2A:
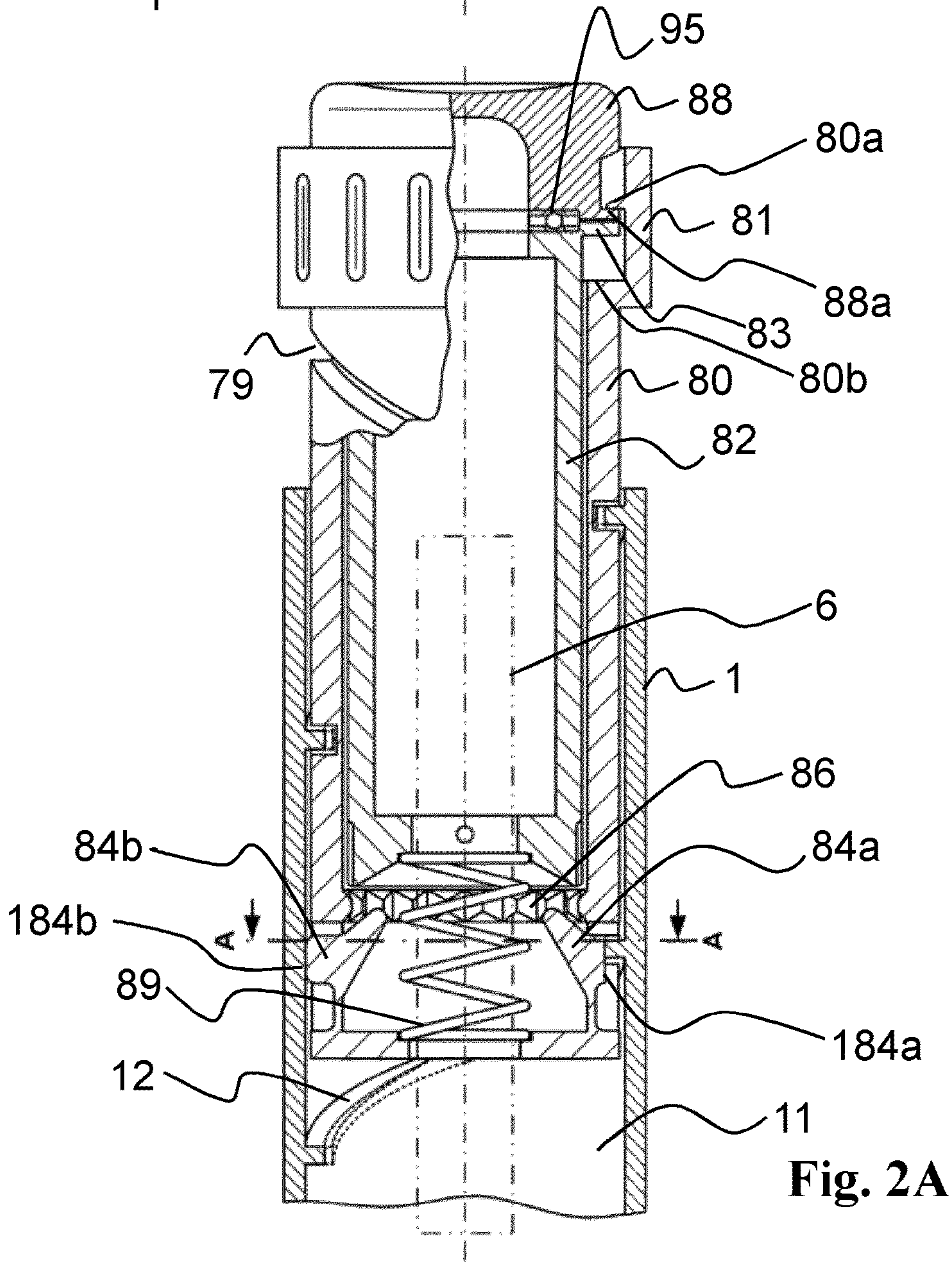
FIG. 2A depicts a longitudinal section of the proximal end of the injection device of FIG. 1 during dose dialing.
Figure 2C:
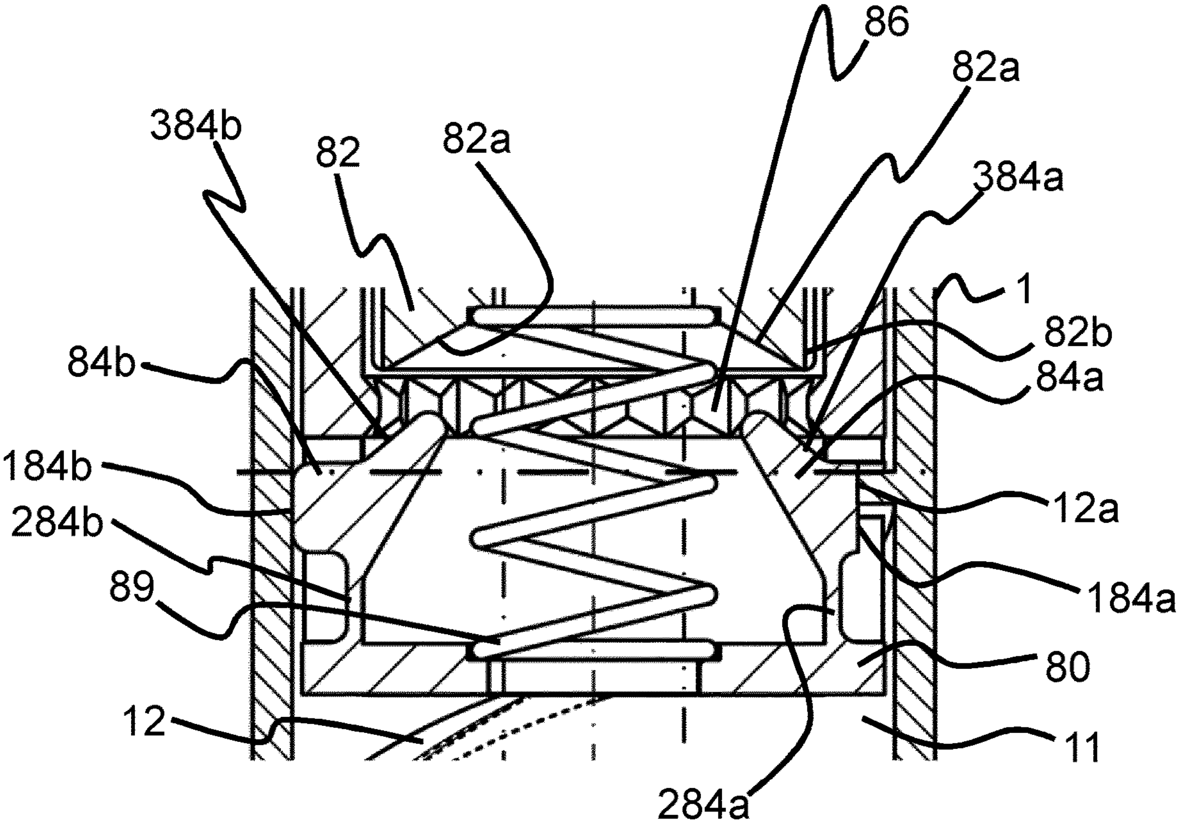
FIG. 2C shows an enlarged section of FIG. 2A.
Figure 2E:
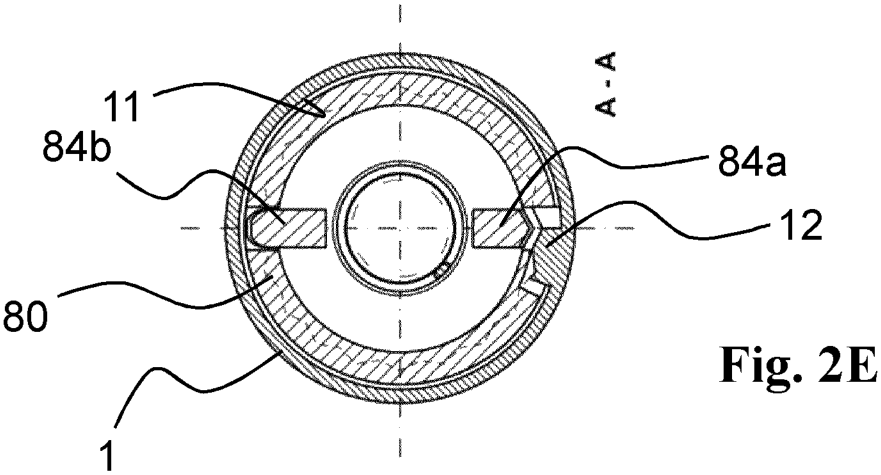
FIG. 2E shows a cross section of the injection device of FIG. 1 during dose dispensing (see A-A in FIG. 2D)
Figure 2D:
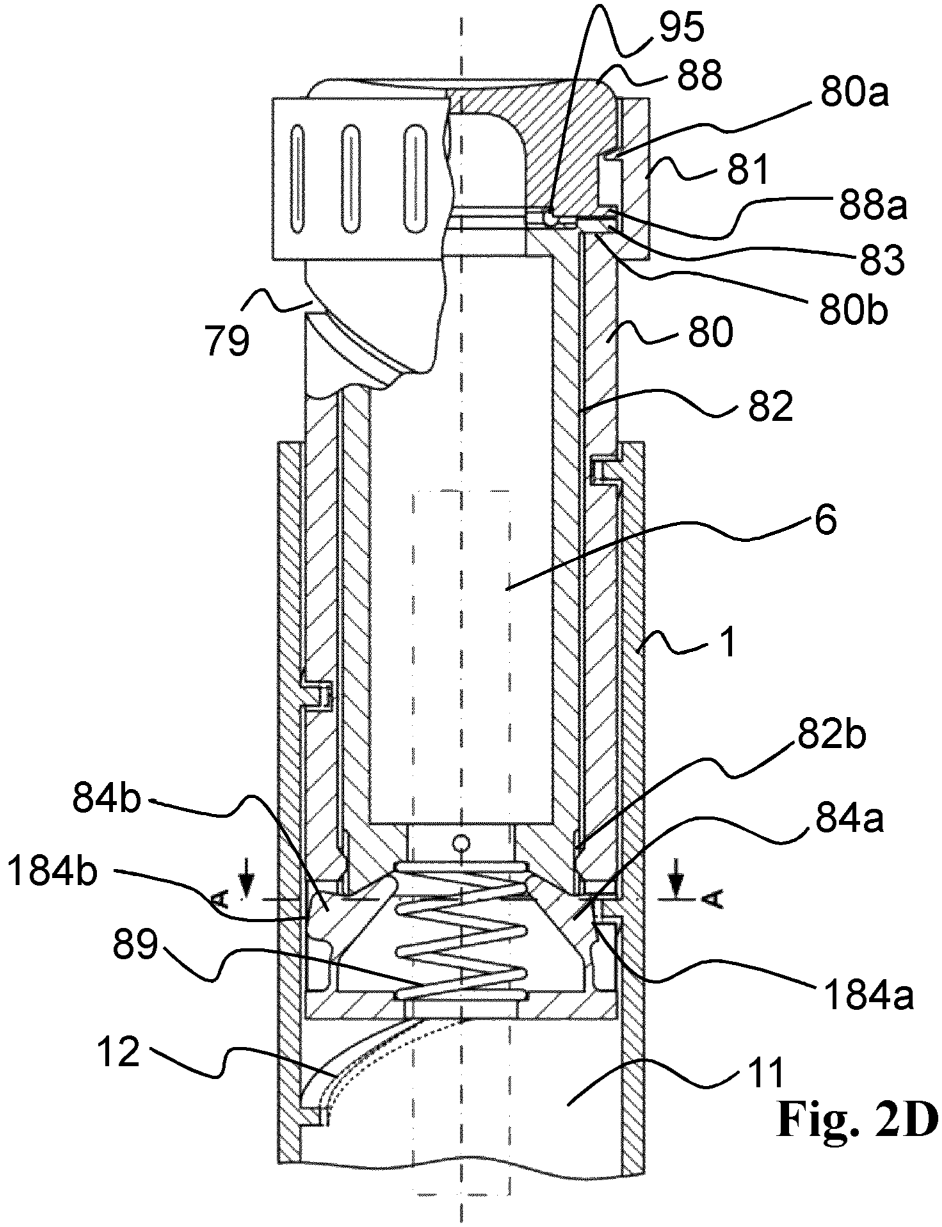
FIG. 2D depicts a longitudinal section of the proximal end of the injection device of FIG. 1 during dose dispensing.

The dial grip 81 is splined to the dose indicator 80, for example by teeth, when in the dialing condition. Alternatively, as shown in FIGS. 2A and 2D the dial grip 81 is one-piece with the dose indicator 80, for example formed by injection molding.

The motional freedom between the dose indicator 80 and the housing 1 is constrained to follow a helical or screwing movement. This is achieved by corresponding mechanical features provided on the dose indicator 80 on one hand side and the inner surface 11 of the housing 1 on the other hand side that mate to form a threaded connection. In the specific situation, the inner surface of the housing is provided with a thread feature in the way of an extended helical rib 12. In the specific situation, the corresponding configuration on the dose indicator for mating with the tread feature on the housing inner surface 11 is a helical groove 79, located at the outer surface of the dose indicator 80. The helical path 79 may have rotational hard stops (not shown) at the respective ends forming a zero dose abutment and a maximum dose abutment for the dose dialed within one dialing step. The dose indicator 80 is marked with a sequence of numbers N in form of a scale at its outer surface, which are visible through the window 18 in the housing 1, to denote the dialed dose of medicament.

The injection button 88 may be formed a plate-like element which is rotatably mounted with a pivot pin 94 journaled in an end wall of the bushing 82. Alternatively, as shown in FIGS. 2A and 2D, the injection button 88 is rotatably coupled to the bushing 82 by means of a bearing 95, for example, a ball bearing. During dose dialing, the injection button 88 moves axially together with the bushing 82 in proximal direction. During dose expelling, the button 88 is pressed by the user's finger axially in distal direction and moves driven by the force of the users finger into the distal direction and does not rotate, wherein the bushing 82 rotates together with the dose indicator 80, the driver tube 85 and the lead screw 6 helically with respect to the housing 1. The bearing 95 allows the rotation of the bushing 82 relative to the injection button 88.

As depicted in FIGS. 2A to 2E a the crest line 12*a* of the projecting helical thread 12 comprises at least along a predefined section a toothing 112, for example gear teeth or saw teeth. Other pointed or rounded toothing forms are possible, as well. In the specific example, the teething is of a regular kind in the sense that the teeth or features are placed adjacently and without suspension, for example by intermittent un-contoured regions. The purpose of the teething 112 is to provide a mechanical interface with a multiple of distinct ratchet features that serve for contact areas in an interacting or meshing engagement with one or more engaging members located in essentially fixed relation to the dose indicator 80. This engagement, in general, is configured to cause a modulation in the dwell torque or frictional counter torque it acts against a relative rotation of the dose indicator 80 and the housing 1. The modulation, at a distinct position, may be in the way of an increase or decrease in the dwell torque that promotes or counteracts a user induced rotation of the aforementioned parts. In instances, the perception of the modulation can provide a user with a tactile indexing feedback. In instances, the indexing feedback may be such that it allows the user to understand where distinct preferred dialing positions are located. In other situations, as shown in the figures, the feedback may be rather designed to give the user a tactile impression when performing a stepwise increase or decrease in dose dialing. The feedback may be provided for convenience reasons but, in instances, the feedback may also be designed to increase safety. In particular, an appropriately defined dose increment overhaul torque may help to prevent unintended changes in dose setting. Unintended dose setting changes could be cause by incautious handling of the dialed injection device during subsequent steps before drug administration. It is not hard to imagine that unexperienced users might touch the injection device at the dose indicator 80 when screwing a needle (not shown) onto the flange, namely thread 5.

It should be apparent, that perceivable indexing appearance requires some torque input. It might therefore be a consideration to provide switchable indexing appearance. This may help to reduce an indexing caused loss in torque output during dose delivery. It should be noted that the torque required for rotating the lead screw has to be created by conversion of the linear user input force along the threaded engagement between the dose indicator and the housing. In the shown embodiment, switching of the indexing is achieved by means of one engaging member 84*a* which is pivotable hinged to the dose indicator 80 in a live hinge or similar bendable structure. In particular, the live hinge is configured to provide a biasing force to the engaging member 84*a* in a radially outward direction. This biasing is configured to urge the engaging member 84*a* into engagement with a teeth (cog) of the teething 112. Accordingly, this contact occurs at the side surface 184*a* of the engaging member 84 which is oriented radially outwards against the crest line of the teething 112 of the thread 12. This is shown in FIGS. 2A, 2B and 2C. The engaging member 84*a* is attached by a neck portion 284*a* located at the distal end of the engaging member 84*a* to the dose indicator 80, wherein the neck portion 284*a* is, for example, pivotably attached to a front surface of a distal end flange of the dose indicator 80 as shown in FIGS. 2A, 2C and 2D. In the specific embodiment, the engaging member 84*a* has a wing-like form with a proximal end and a sloping surface 384*a* extending from the proximal end of the wing-like form.

In the specific embodiment, the dose indicator 80 further comprises at least one second pivotable member 84*b* which is located, as shown, radially opposite to the slider member 84*a*. Very similar to the engaging member 84*a*, the slider member 84*b* has a wing-like form In difference to the engaging member 84*a*, the slider member 84*b* does not engage with the teething 112 of the thread 12 but rather abuts against a cylindrically shaped portion of the inner surface 11. The contact region of the slider member 84*b* may be provided as a slightly rounded side surface 184*b* projecting radially outwards. This is shown in FIGS. 2A to 2C. In the outlined situation, the slider member 84*b* is expected to produce approximately the opposite radial reaction force to the dose indicator 80 as the engaging member 84*a* produces to thereby maintain the dose indicator 80 in a center axis balanced force situation. The second pivotable member 84*b* is attached to the front surface of the distal end flange of the dose indicator 80 by a second live hinge 284*b*. Both, namely the engaging member 84*a* and the slider member 84*b* have tapered rounded heads defining protruding distally into the interior space of a teethed bore 86 in the dose indicator 80. The rounded heads define two radially outward facing sloping surfaces 384*a*, 384*b* that allow contact of a tapered surface to deflect the members 84*a*, 84*b* radially inwards.

Additionally, the dose indicator 80 comprises a compression spring 89 located between the front surface of the distal end flange of the dose indicator 80 at its distal end and an opposite distal front surface of the bushing 82 and presses the flange 83 of the bushing 82 and/or an outer flange 88*a* of the injection button 88 against a flange 80*a* projecting from the inner surface of the dial grip 81 or the dose indicator 80.

Alternatively or additionally, a biasing element, for example at least two Belleville spring washer, may be provided between a flange 80*b* at the housing (see FIGS. 2A and 2D) and the flange 83 of the bushing 82 (not shown).

The bushing 82 comprises at its distal end a sloping surface 82*a* forming a cone-like surface (see FIG. 2C). Further, the outer surface of the bushing 82 comprises at its distal end longitudinal grooves 82*b* (see FIGS. 2C and 2D).

With the device in the "at rest" condition, the dose indicator 80 is positioned at its initial position, for example with its zero dose abutment against the zero dose abutment of the housing 1 and the injection button 88 is not depressed, i.e. in the position shown in FIG. 1A. Dose marking (number) '0' on the dose indicator 80 is visible through the window 18 of the housing 1.

The user selects a variable dose of the medicament by rotating the dial grip 81 clockwise, which generates an identical rotation of the dose indicator 80 by the connection to the housing 1 via thread 12 and helical path 79. The dose indicator 80 with the dial grip 81, the injection button 88 screws out and the bushing 82 is thereby lifted away from the proximal end of the housing 1 (see FIG. 1B), wherein the axial distance moved by the bushing 82 into proximal direction corresponds to the axial distance over which the dose indicator is screwed out.

As the dose indicator 80 rotates, each projecting pin 101 of the bushing 82 translates along the respective longitudinal groove 100 of the driver tube 85 into proximal direction taken along by the axial force of the compression spring 89, wherein the driver tube 85 is locked against clockwise rotation by radial protrusions at a clicker arm 85*a* which are biased toward the inner side wall of the insert 40. Neither the driver tube 85 nor the lead screw 6 undergo any type of motion relative to the housing during dose dialing.

If a set dose is reduced by rotating the dose setting button 81 in an anti-clockwise direction the pawl mechanism working between the driver tube 85 and the housing 1 (radial protrusion at clicker arm 85*a*) is sufficient reluctant to rotate in its non-blocking direction to prevent the bushing 82 and driver tube 85 from following this anti-clockwise rotation. As in this situation each pin 101 of bushing 82 travels along the groove 100 into distal direction the movement of the dose indicator 80 and the bushing 82 is reversed from the movement described above.

By the rotation of the dose setting button 81 in any direction the cog or tooth on the side surface 184*a* of the pivotable engaging member 84*a* of the dose indicator 80 clicks from one recess between two of the teeth of the teething 112 at the thread 12 to the next one, the recesses may be so spaced that one click corresponds to a pre-defined change of the set dose, e.g. one unit or one half unit. As the user rotates the dial grip 81 sufficiently to increment the mechanism by one increment, the dose indicator 80 rotates relative to the housing 1 by one recess. At this point the protrusion (cog or tooth on the side surface 184 of the engaging member 84*a*) re-engage into the next settled position. Depending on the shape of the teething 112 and the engaging member 84*a*, an audible click may be generated by the tooth overhaul, and tactile feedback is given by the change in torque input.

The user may further increase the selected dose by continuing to rotate the dial grip 81 in the clockwise direction. The process of overhauling the teeth of the teething 112 is repeated for each dose increment. If the user continues to increase the selected dose until the maximum dose limit for one selected medicament dose (not shown) is reached, the dose indicator 80 may reach the maximum dose abutment when provided on the housing 1 and thereby prevent further rotation of the dose indicator 80 in this direction.

The compression spring 89 may be attached to the dose indicator 80 and slides with its proximal end along the distal front surface of the bushing 82 during dose dialing. Alternatively, the compression spring 89 is attached to the bushing 82 and slides along the dose indicator 80 during dose dialing. It is a purpose of the compression spring 89 to maintain the bushing 82 in a distally retracted position relative to the dose indicator 80 wherein no engagement of the internal teeth 86 in the bore of the dose indicator 80 and on the external teeth 82*b* on bushing occurs and the dose indicator 80 is allowed to rotate without driving the bushing 82.

With the mechanism in a state in which a dose has been selected, the user is able to deselect any number of increments from this dose. Deselecting a dose is achieved by the user rotating the dial grip 81 anti-clockwise.

When the injection button 88 is pressed to inject (dispense) the set dose the bushing 82 will follow the anti-clockwise rotation of the dial grip 81 which is induced by the thread engagement between the helical path 79 of the dose indicator 80 and the thread feature 12 at the inner side of the housing 1 when the dose indicator 80 is pressed back into the housing 1. Before this rotation starts, a splined connection is created between the dose indicator 80 and the bushing 82 to cause the bushing 82 for rotating together with the dose indicator 80. In the embodiment, the splined connection is provided by the grooves 82*b* of the bushing 82 engaging the teeth between two neighboring grooves 86 at the inner wall of the dose indicator 89 (see FIG. 2D). In view of this aforementioned switching in the drivetrain configuration it is useful to understand that the spring 89 may be configured such as to allow engagement of the splined connection before the dose indicator 80 starts rotating. This can, for example, be achieved by making the spring rate and bias such that the linear force required for overcoming the spring 89 until splined engagement occurs is not sufficient, when converted into a torque, for rotating the dose indicator 80 away from the presently settled index engagement between the teething 12 and the engaging member 84*a*. In a more elaborated variant with intermittent teething 112 the forces may be arranged such as to create the above locking effect only in a position of the dose indicator 80 where a ratchet feature 112 engagement occurs. In the intermittent positions the dose indicator 80 would be driven towards the next ratchet feature 112 engagement without driving the bushing 82 to this extent. At the ratchet feature engagement, the mechanism would behave as explained before, namely by engaging the splined connection between dose indicator 80 and bushing 82 before subsequent rotation takes place.

By pressing the injection button 88 the injection button 88 and with it the bushing 82 move into distal direction relative to the dose indicator 80 against the force of the compression spring 89 until the flange 83 of the bushing and/or the flange 88*a* of the injection button 88 abuts the second flange 80*b* of the dose indicator 80 (see FIG. 2D). By the displacement of the bushing 82 the engaging member 84*a* and the slider member 84*b* are deflected radially inwards by abutment of the sloping surface 82*a* of the bushing 82 against the sloping surfaces 384*a*, 384*b* of the engaging member 84*a* and the slider member 84*b*. The deflection of the engaging member 84*a* causes disengagement of the engaging member 84 from the teething 112. The slider member 84*b* is deflected, as well, thereby maintaining the balance in reaction forces on the bushing 82 and thereby avoiding creation of any tilting torque on the bushing 82 relative to the dose indicator 80 (see FIGS. 2D and 2E). The deflection axis are configured to extend, for example, essentially perpendicular to the longitudinal axis of the injection device. Further, the displacement of the bushing 82 into distal direction causes an engagement of the grooves 82*b* at the outer surface of the bushing 82 and the teeth forming the grooves 86 at the inner surface of the dose indicator 80 thereby coupling the dose indicator 80 and the bushing 82 so that both elements rotate together. In one embodiment the longitudinal force necessary to compress the compression spring 89 is configured such that first the grooves 82*b* at the outer surface of the bushing 82 engage the teeth forming the grooves 86 at the inner surface of the dose indicator 80 and after engagement the longitudinal force provided by the user to the injection button 88 is transmitted via the dose indicator 80, the bushing 82, the driver tube 85 to the lead screw 6 in order to inject the dialed medicament dose.

Tactile feedback during dose dispense may be provided via compliant cantilever clicker arm 85*a* integrated into the distal end of the driver tube 85 as shown in FIG. 2. This arm 85*a* interfaces radially with ratchet features on the inner surface of the insert 40, whereby the ratchet tooth spacing corresponds to the dose indicator 80 rotation required for a single increment dispense. During dispense, as the driver tube 85 rotates, the ratchet feature engages with the clicker arm 85*a* to produce an audible click with each dose increment delivered. The clicker arm 85*a* is further adapted such that it prevents rotation of the lead screw during dose dialing.

Delivery of a dose continues via the mechanical interactions described above while the user continues to depress the injection button 88. If the user releases the injection button 88, the delivery of a dose is halted.

Once the delivery of a dose is stopped, by the dose indicator 80 returning to the zero dose abutment within the housing 1, the user may release the injection button 88. The mechanism is now returned to the “at rest” condition, in particular the dose indicator 80 is returned to its initial position (zero position, see FIG. 1A).

In one embodiment at the end of dose, additional audible feedback may be provided in the form of a “click”, distinct from the “clicks” provided during dispense, to inform the user that the device has returned to its zero position.

Figure 3:
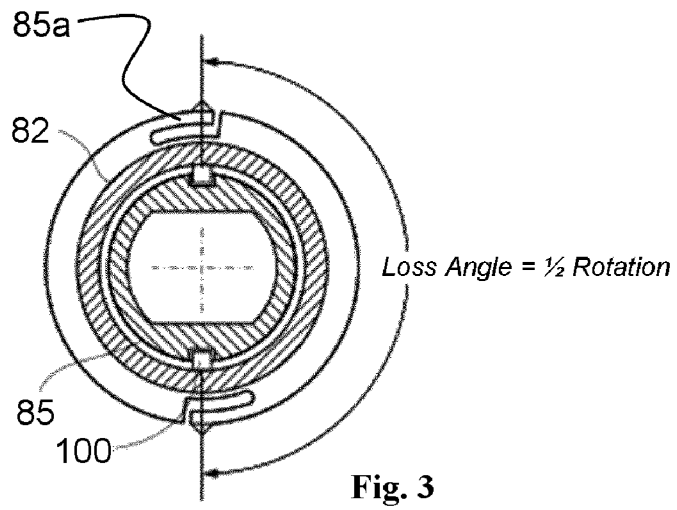
FIG. 3 shows a cross section of the drive member of the injection device of a second embodiment of an injection device (see A-A in FIG. 4)
Figure 4:
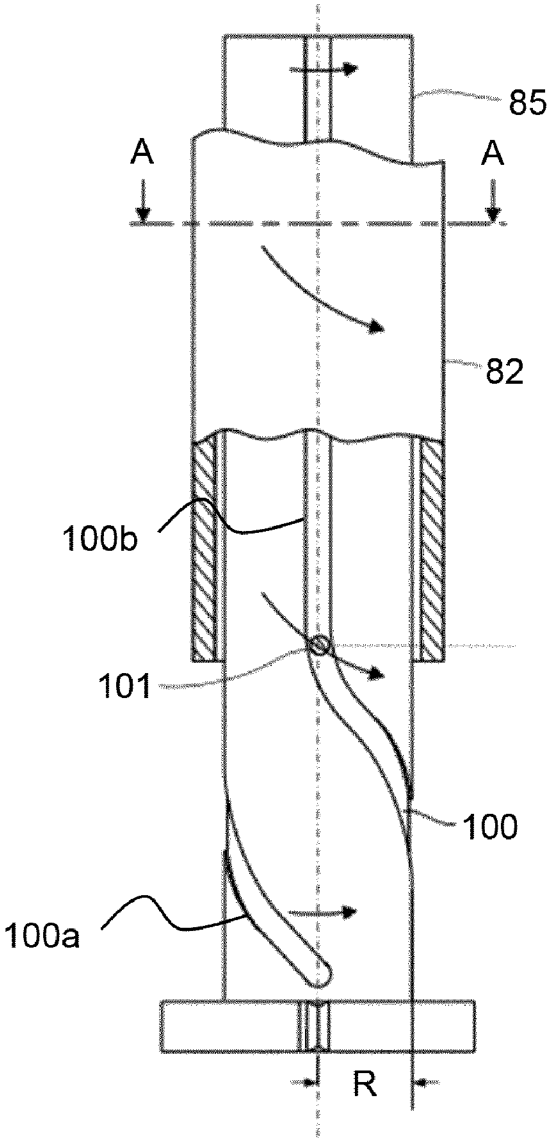
FIG. 4 depicts a partly cut away side view of the drive member of FIG. 3.
Figure 5:
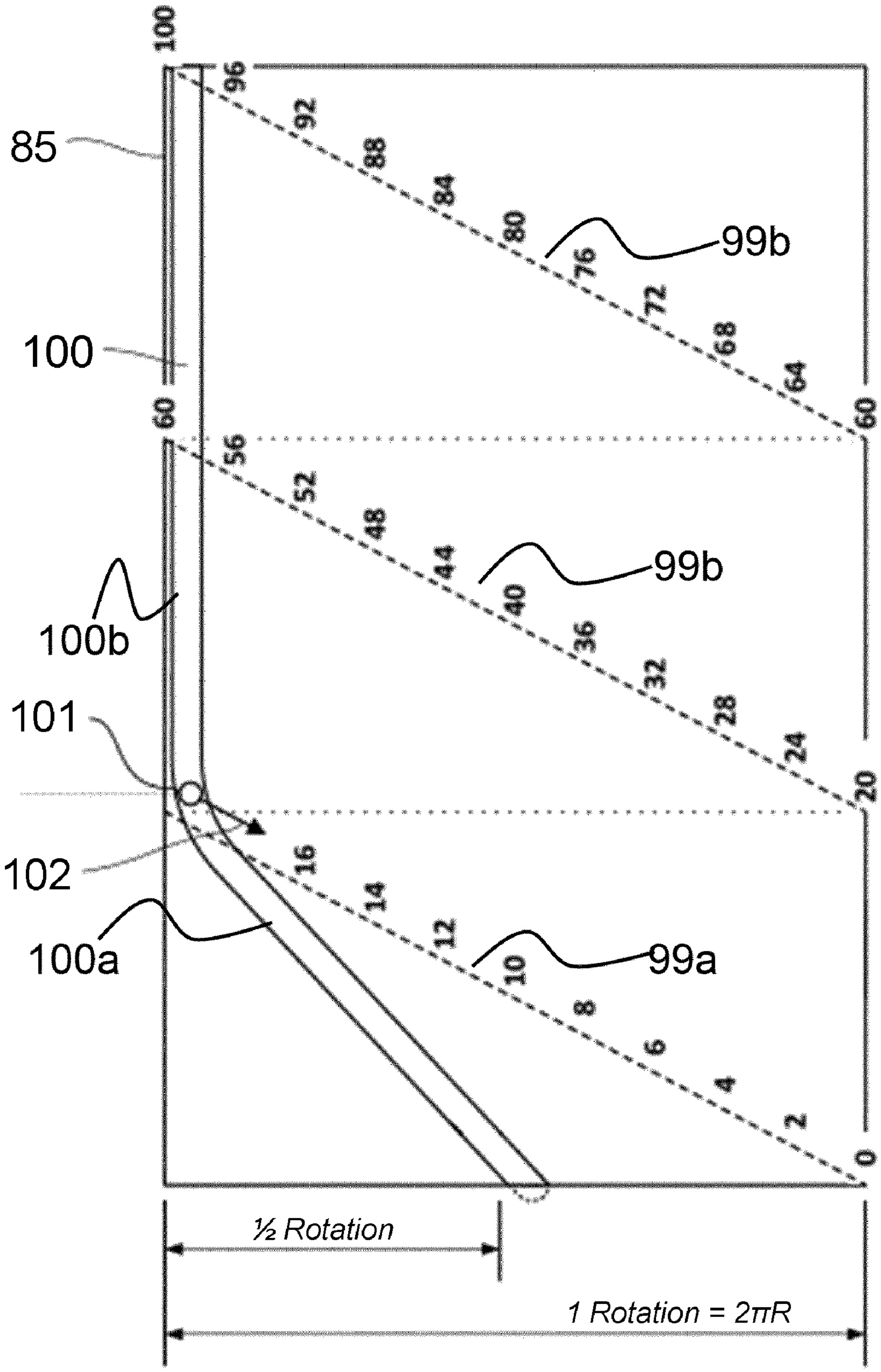
FIG. 5 shows the unrolled surface of one element of the drive member of FIG. 3.

In a second embodiment shown in FIGS. 3 to 5 corresponds to the embodiment shown in FIGS. 1A to 2D but each groove 100 of the driver tube 85 has a first section 100*a* at its distal end and a second section 100*b* at its proximal end, wherein the second section 100*b* is a straight groove traveling parallel to the longitudinal axis of the device. The first section 100*a* of the groove 100 is a helical groove providing a half revolution with the same handedness as a helical path 79 of the dose indicator 80. Concerning the embodiment shown in FIGS. 1A to 2D the helical path 79 of the dose indicator 80 and the first section 100*a* of the groove 100 both are left-handed. To some extent the groove 100 forms a two-start-thread but a one-start-thread or a three-start-thread is possible as well depending on the number of pins 101 of the bushing 82.

Correspondingly, as one can derive from FIG. 5, the second embodiment of the injection device comprises a scale with numbers N having a first section 99*a* of the scale covering the numbers 0 to 19 and a second section 99*b* of the scale covering the numbers 20 to 100. The numbers of the first section of the scale are shown through window 18 of the housing 1 during the first revolution of the dose indicator 80 (i.e. the first 360° of the rotation, the first rotation angle section) and the numbers of the second section of the scale are shown during the second and the third revolution of the dose indicator 80 (i.e. >360° to 1080° of the rotation, the second rotation angle section). Accordingly, during the first rotation angle section of the dose indicator 80 the dose can be dialed with the double resolution compared with the second rotation angle section of the dose indicator 80.

As the dose indicator 80 rotates, each projecting pin 101 of the bushing 82 translates along the respective longitudinal groove 100 of the driver tube 85 into proximal direction taken along by the projecting flange 83, wherein the groove 100 comprises the first section 100*a* and the second section 100*b*. The pitch of the first groove section 100*a* is approximately 45°, whereas the pitch of the second groove section 100*b* is 0°.

During the first revolution of the dose indicator 80, i.e. in this embodiment the first rotation angle section of 360° from the initial position (zero position), the full revolution of the dose indicator 80 is transformed into a half revolution of the bushing 82 backwards caused by the helical groove section 100*a* and the axial (helical) translation of the dose indicator 80 with the length I/2 compared with the lead I of the helical thread 79 of the dose indicator 80. To some extend the first helical groove section 100*a* thereby provides a loss angle of 180° or a half revolution (see FIG. 3). Accordingly, the transformation ratio increases from the first rotation angle section to the second rotation angle section. This allows a higher resolution for dose dialing during the first rotation angle section of—in this embodiment—360° using the dose indicator 80. During dialing within the first rotation angle section of the dose indicator 80 the numbers N of the first scale section 99*a* are shown within window 18.

After the first revolution (full turn) of the dose indicator 80 each pin 101 arrives at the second section 100*b* of the groove 100. In this section the bushing 82 is kept non-rotated with regard to the driver tube 85 due to its coupling to the driver tube 85 by the straight axial second section 100*b* of the groove 100. Accordingly, during the second rotation angle section covering the range >360° to 1080° the axial (helical) translation of the dose indicator corresponds to the lead I of the helical thread 79 of the dose indicator 80. Hence, the resolution for dose dialing is half of the resolution provided during the first rotation angle section of the dose indicator 80. During dialing within the second rotation angle section of the dose indicator 80 the numbers N of the second scale section 99*b* are shown within window 18.

During dose injection, each pin 101 travels along its corresponding groove 100 into opposite (distal) direction compared with dose dialing. Accordingly, when passing the first groove section 100*a* only half of the dose per one revolution is dispensed due to the helical form of the groove compared with the second groove section 100*b*.

With higher pitch angle the pin 101 is not sufficiently supported by the rim of the groove 100. This is demonstrated in FIG. 5. The resulting sliding force depicted by arrow 102 is almost parallel to the rim of the groove 100 within the first groove section 100*a*. The force fraction normal to the rim of the groove 100 is higher within the second groove section 100*b* having a smaller pitch. However, the accuracy of dose dialing is provided by the ratchet engagement of the teething 112 of the thread 12 at the housing 1 and the engaging member 84*a*.

With regard to the second embodiment, the inner toothing at the insert 40 has smaller teeth with a pitch of half of the pitch in the first embodiment explained above. The ratchet teething at the insert is thereby able to match with the increased resolution of the mechanism during high-resolution dose expelling, namely when the pin 101 travels along the helical first section 100*a* of the groove 100.

For the first and second embodiments the form of the teething 112 of the thread 12 may be adapted to a different dose amount per rotation angle of the dial grip 81 or different mechanism behavior at different rotation angle. Accordingly, the teeth form may be adapted to the dialed (and dispensed) dose for each (absolute) rotation angle section. This adequate feedback improves dose dialing for the user.

REFERENCE NUMBERS

1 housing
2 cartridge holder
2*a* window in cartridge holder 2
3 cartridge
4 cap
5 thread
6 lead screw
7 thread of the lead screw 6
11 inner surface of housing 1
12 thread projecting from inner surface 11 of housing 1
12*a* front surface of thread 12
18 window of the housing 1
40 insert
79 helical path
80 dose indicator
80*a* first flange
80*b* second flange
81 dial grip
82 bushing
82*a* sloping surface of bushing 82
82*b* groove
83 flange of bushing 82
84*a* engaging member
84*b* slider member
85 driver tube
85*a* clicker arm
86 groove
87 radial protrusion
88 injection button
88*a* flange
89 compression spring
94 pivot pin
95 bearing
99*a* first scale section
99*b* second scale section
100 groove
100*a* first groove section
100*b* second groove section
101 pin
102 arrow
112 toothing
184*a* side surface of engaging member 84*a*
184*b* side surface of slider member 84*b*
284*a* side surface of engaging member 84*a*
284*b* side surface of slider member 84*b*
384*a* sloping surface of engaging member 84*a*
384*b* sloping surface of slider member 84*b*
N number of the scale

The invention claimed is:

1. An injection device for selecting and dispensing a number of user variable doses of a liquid drug or medicament formulation, the injection device comprising:

a housing defining an internal space with an inner surface, the inner surface being provided with a thread feature and multiple distinct ratchet features spread along a helical path;

a dose indicator positioned within the internal space of the housing, the dose indicator having an external surface configured to mesh or engage with the thread feature for restricting a motional freedom of the dose indicator within the housing to follow a helical or screwing movement during a dose dialing and a dose dispensing, the dose indicator further comprising a number of engaging members, at least one of the engaging members being configured to contact the multiple distinct ratchet features in distinct positions during the helical or screwing movement, wherein the distinct positions correspond to a plurality of dosage amounts and the contact is configured to provide a user with a tactile feedback by increasing or decreasing a dwelling torque at each of the distinct positions, and wherein the engaging members are resiliently biased towards a distant position; and a release mechanism connected to the dose indicator, the release mechanism being configured to, when activated during the dose dispensing, urge the engaging members away from the distant position and against a force of the resilient bias thereby suspending the tactile feedback at least for a subset of the multiple distinct positions.

2. The injection device of claim 1, wherein the thread feature is a helical thread, and the multiple distinct ratchet features are integrated with the helical thread.

3. The injection device of claim 2, wherein the multiple distinct ratchet features are integrated with the helical thread as a profiled crest line or as a shoulder of the helical thread.

4. The injection device of claim 1, wherein the multiple distinct ratchet features are provided as a series of teeth, notches or detent features that are arranged along a helical path on the internal surface or integrated with the helical path of the thread feature.

5. The injection device of claim 1, wherein the resilient bias of the engaging members towards the distant position is appropriate for contacting the multiple distinct ratchet features.

6. The injection device of claim 1, wherein each engaging member includes at least one live hinge, and the resilient bias of the engaging members is achieved by a combined elasticity of the live hinges of the number of engaging members.

7. The injection device of claim 1, wherein the tactile feedback is suspended by reducing the dwelling torque to a uniform lower value.

8. The injection device of claim 1, wherein the release mechanism comprises a drive member, the drive member being located within the dose indicator and comprising a first sleeve-like element that is axially displaceable relative to the dose indicator during the dose dispensing.

9. The injection device of claim 8, wherein the dose indicator further comprises at least one slider member, wherein a pivotable member is adapted to support the first sleeve-like element during axial displacement of the first sleeve-like element relative to the dose indicator.

10. The injection device of claim 8, wherein during the dose dispensing, the dose indicator is rotatably fixed with regard to the first sleeve-like element, wherein the drive member comprises a second sleeve-like element positioned within the first sleeve-like element, wherein the second sleeve-like element is splined to a lead screw, and wherein the first sleeve-like element is coupled to the second sleeve-like element by a connection comprising a pin and a groove, wherein the pin moves along the groove during the dose dialing and the dose dispensing.

11. The injection device of claim 10, wherein the groove provides a first pitch along a first section of the groove and a second pitch along a second section of the groove, wherein the first pitch is different from the second pitch.

12. The injection device of claim 10, wherein the lead screw is rotatably coupled with the housing during the dose dispensing and is axially and rotatably fixed with regard to the housing during the dose dialing.

13. The injection device of claim 8, wherein the drive member effects a change in a transformation ratio between a rotation and a longitudinal shift of the dose indicator with regard to the housing such that within a first rotation angle section the rotation of the dose indicator is transformed with a first transformation ratio and within at least a second rotation angle section the rotation of the dose indicator is transformed with a second transformation ratio.

14. The injection device of claim 8, further comprising an injection button coupled to a proximal end of the dose indicator, wherein the injection button is adapted to be pressed into a distal direction for the dose dispensing thereby axially displacing the first sleeve-like element relative to the dose indicator.

15. The injection device of claim 8, wherein at least one of the engaging members has a wing-like form, and wherein a sloping surface at a proximal end of the wing-like form is adapted such that a corresponding sloping surface at a distal end of the first sleeve-like element engages the sloping surface of the wing-like form during the dose dispensing and after an axial displacement of the first sleeve-like element thereby urging the engaging member away from the distant position.

16. The injection device of claim 8, wherein the dose indicator comprises a scale at an outer surface of the dose indicator showing a dialed dose to the user through a window or an opening within the housing.

17. The injection device according to claim 16, wherein the drive member effects a change in a transformation ratio between a rotation and a longitudinal shift of the dose indicator with regard to the housing such that within a first rotation angle section the rotation of the dose indicator is transformed with a first transformation ratio and within at least a second rotation angle section the rotation of the dose indicator is transformed with a second transformation ratio, and wherein the scale comprises a first scale section corresponding to the first rotation angle section and a second scale section corresponding to the second rotation angle section, wherein a graduation of the first scale section is different from a graduation of the second rotation angle section.

18. The injection device of claim 1, wherein at least one of the engaging members has a wing-like form with a wing-like portion, wherein:

the wing-like portion is integrated with the dose indicator thereby defining a live hinge with a pivot axis located at the live hinge, or a side surface of the wing-like form is oriented radially outwards is adapted to engage with the multiple ratchet features.

19. The injection device of claim 1, wherein the multiple distinct ratchet features include a first subset of ratchet features having a first profile form and a second subset of ratchet features having a second profile form, wherein the first profile form is different from the second profile form.

20. The injection device of claim 1, further comprising a cartridge containing a liquid medicament.

21. An injection device for selecting and dispensing a number of user variable doses of a liquid drug or medicament formulation, the injection device comprising:

a housing defining an internal space with an inner surface, the inner surface being provided with a thread feature and multiple distinct ratchet features spread along a helical path;

a dose indicator positioned within the internal space of the housing, the dose indicator having an external surface configured to mesh or engage with the thread feature for restricting a motional freedom of the dose indicator within the housing to follow a helical or screwing movement during a dose dialing and a dose dispensing, the dose indicator further comprising a number of engaging members, at least one of the engaging members being configured to contact the multiple distinct ratchet features in distinct positions during the helical or screwing movement, wherein the contact is configured to provide a user with a tactile feedback by increasing or decreasing a dwelling torque at each of the distinct positions, and wherein the engaging members are resiliently biased towards a distant position;

a release mechanism connected to the dose indicator, the release mechanism being configured to, when activated during the dose dispensing, urge the engaging members away from the distant position and against a force of the resilient bias thereby suspending the tactile feedback at least for a subset of the multiple distinct positions, wherein the release mechanism comprises a drive member, the drive member being located within the dose indicator and comprising a first sleeve-like element that is axially displaceable relative to the dose indicator during the dose dispensing;

wherein during the dose dispensing, the dose indicator is rotatably fixed with regard to the first sleeve-like element;

wherein the drive member comprises a second sleeve-like element positioned within the first sleeve-like element, wherein the second sleeve-like element is splined to a lead screw, the lead screw rotatably coupled with the housing during the dose dispensing and is axially and rotatably fixed with regard to the housing during the dose dialing;

wherein the first sleeve-like element is coupled to the second sleeve-like element by a connection comprising a pin and groove, wherein the pin moves along the groove during the dose dialing and the dose dispensing; and wherein the groove provides a first pitch along a first section of the groove and a second pitch along a second section of the groove, wherein the first pitch is different from the second pitch.

22. An injection device for selecting and dispensing a number of user variable doses of a liquid drug or medicament formulation, the injection device comprising:

a housing defining an internal space with an inner surface, the inner surface being provided with a thread feature and multiple distinct ratchet features spread along a helical path;

a dose indicator positioned within the internal space of the housing, the dose indicator having an external surface configured to mesh or engage with the thread feature for restricting a motional freedom of the dose indicator within the housing to follow a helical or screwing movement during a dose dialing and a dose dispensing, the dose indicator further comprising a number of engaging members, at least one of the engaging members being configured to contact the multiple distinct ratchet features in distinct positions during the helical or screwing movement, wherein the contact is configured to provide a user with a tactile feedback by increasing or decreasing a dwelling torque at each of the distinct positions, and wherein the engaging members are resiliently biased towards a distant position;

a release mechanism connected to the dose indicator, the release mechanism being configured to, when activated during the dose dispensing, urge the engaging members away from the distant position and against a force of the resilient bias thereby suspending the tactile feedback at least for a subset of the multiple distinct positions;

wherein the release mechanism comprises a drive member, the drive member being located within the dose indicator and comprising a first sleeve-like element that is axially displaceable relative to the dose indicator during the dose dispensing; and wherein at least one of the engaging members has a wing-like form, and wherein a sloping surface at a proximal end of the wing-like form is adapted such that a corresponding sloping surface at a distal end of the first sleeve-like element engages the sloping surface of the wing-like form during the dose dispensing and after an axial displacement of the first sleeve-like element thereby urging the engaging member away from the distant position.

* * * * *